(12) United States Patent
Branchini et al.

(10) Patent No.: US 7,807,429 B2
(45) Date of Patent: Oct. 5, 2010

(54) ISOLATED LUCIFERASE GENE OF L. ITALICA

(75) Inventors: Bruce R. Branchini, Old Lyme, CT (US); Tara L. Southworth, Norwich, CT (US); Jennifer P. DeAngelis, Whitestone, NY (US); Aldo Roda, Bologna (IT); Elisa Michelini, Bologna (IT)

(73) Assignee: Connecticut College, New London, CT (US)

( * ) Notice: Subject to any disclaimer, the term of this patent is extended or adjusted under 35 U.S.C. 154(b) by 622 days.

(21) Appl. No.: 11/702,819

(22) Filed: Feb. 6, 2007

(65) Prior Publication Data

US 2007/0190587 A1 Aug. 16, 2007

Related U.S. Application Data

(60) Provisional application No. 60/772,804, filed on Feb. 13, 2006.

(51) Int. Cl.
*C12N 9/02* (2006.01)
(52) U.S. Cl. ...................................... 435/189; 536/23.2
(58) Field of Classification Search .................. None
See application file for complete search history.

(56) References Cited

U.S. PATENT DOCUMENTS

| 4,968,613 | A | 11/1990 | Masuda et al. ............ 435/172.3 |
| 5,219,737 | A | 6/1993 | Kajiyama et al. |
| 5,229,285 | A | 7/1993 | Kajiyama et al. ............ 435/189 |
| 6,132,983 | A | 10/2000 | Lowe et al. ..................... 435/8 |
| 6,387,675 | B1 | 5/2002 | Wood et al. ................. 435/189 |
| 6,451,549 | B1 | 9/2002 | Escher et al. |
| 6,495,355 | B1 | 12/2002 | Contag et al. ............... 435/189 |
| 6,812,012 | B1 | 11/2004 | Hattori et al. ............... 435/189 |
| 2002/0138855 | A1 | 9/2002 | Zhang et al. |
| 2004/0224377 | A1 | 11/2004 | Hawkins et al. |

FOREIGN PATENT DOCUMENTS

WO          00/24878      *  5/2000

OTHER PUBLICATIONS

J. Sommer et al. "In vivo Import of Firefly Luciferase into the Glycosomes of *Trypanosoma brucei* and Mutational Analysis of the C-terminal Targeting Signal", Mol. Biol. Cell 3:749-759 (1992).*
S.V. Mamaev et al. "Firefly Luciferase: Alteration of the Color of Emitted Light Resulting from Substitutions at Position 286", J. Am. Chem. Soc. 118:7243-7244 (1996).*
Devine, Jerry H., et al. "*Luciferase from the East European firefly Luciola mingrelica*: cloning and nucleotide sequence of the cDNA, overexpression in Escherichia coli and purification of the enzyme", Biochimica and Biophysica Acta, vol. 1173, pp. 121-132 (1993).
Roda, Aldo, et al. "*Biotechnological applications of bioluminescence and chemiluminescence*", Trends in Biotechnology, vol. 22, No. 6, pp. 295-303 (2004).
Branchini, Bruce R., "*Luciferase from the Italian firefly Luciola italica: Molecular cloning and expression*", Comparative Biochemistry and Physiology, part B, vol. 145, pp. 159-167 (2006).
"*Spectral Emission and Quantum Yield of Firefly Bioluminescence*," by H. H. Seliger, et al., Arch. Biochem. Biophys. vol. 88, pp. 136-141 (1960).
"*The Chemi- and Bioluminescence of Firefly Luciferin: An Efficient Chemical Production of Electronically Excited States*," by E. H. White, et al., Bioorg. Chem. vol. 1, 92-122 (1971).
"*Firefly Luciferase*," by M. DeLuca, Adv. Enzymol. vol. 44, pp. 37-68 (1976).
"*Bioluminescence of the firefly: Key steps in the formation of the electronically excited state for model systems*," by J.-Y. Koo, et al., Proc. Natl. Acad. Sci. USA, vol. 75, No. 1, pp. 30-33 (1978).
"*Bioluminescence*," by J. W. Hastings, Cell Physiology Source Book, Academic Press, New York, pp. 665-681 (1995).
"*The Chemical Mechanism and Evolutionary Development of Beetle Bioluminescence*," by K. V. Wood, Photochemistry and Photobiology, vol. 62, No. 4, pp. 662-673 (1995).
"*Firefly Luciferase as a Tool in Molecular and Cell Biology*," by S. J. Gould, et al., Anal. Biochem., vol. 175, pp. 5-13 (1988).
"*Advances in In Vivo Bioluminescence Imaging of Gene Expression*," by C. H. Contag, et al., Annu. Rev. Biomed. Eng., vol. 4, pp. 235-260 (2002).
"*Development of safe and efficient novel nonviral gene transfer using ultrasound: enhancement of transfection efficiency of nakes plasmid DNA in skeletal muscle*,", by Y. Taniyama, et al., Gene Therapy, vol. 9, pp. 372-380 (2002).
"*Imaging of light emission from the expression of luciferases in living cells and organisms: a review*," by L. F. Greer, III, et al., Luminescence, vol. 17, pp. 43-74 (2002).
"*Stable suppression of gene expression by RNAi in mammalian cells*," by P. J. Paddison, et al., Proc. Natl. Acad. Sci. USA, vol. 99, pp. 1443-1448 (2002).
"*Fast and sensitive multiple sequence alignments on a microcomputer*," by D. G. Higgins, et al., Computer Applications in the Biosciences, vol. 5, pp. 151-153 (1989).
"*Bioluminescence and Chemiluminescence*," by A. Lundin, et al., Methods in Enzymology, Academic Press, New York, vol. 305, pp. 346-370 (2000).
"*A Review of Bioluminescent ATP Techniques in Rapid Microbiology*," by P. E. Stanley, Journal of Bioluminescence and Chemiluminescence, vol. 4, pp. 375-380 (1989).
"*ATP Determination with Firefly Luciferase*," by F. R. Leach, Journal of Applied Biochemistry, vol. 3, pp. 473-517 (1981).
"*Clinical and Biochemical Applications of Luciferases and Luciferins*," by L. J. Kricka, Analytical Biochemistry, vol. 175, pp. 14-21 (1988).
"*Rational and Random Mutagenesis of Firefly Luciferase to Identify an Efficient Emitter of Red Bioluminescence*," by B. R. Branchini, et al., Proc. of SPIE, Genetically Engineered and Optical Probes for Biomedical Applications II, vol. 5329, pp. 170-177 (2004).

* cited by examiner

*Primary Examiner*—Rebecca Prouty
(74) *Attorney, Agent, or Firm*—Todd E. Garabedian; Wiggin and Dana LLP

(57) ABSTRACT

The present invention relates to an isolated nucleic acid and polypeptide sequence that encodes for a luciferase of *Luciola italica*, as well as mutants thereof. The luciferase proteins of the present invention have been found to have extended bioluminescence emission that is red- or blue-shifted, and are useful as a bioluminescent marker or as an additive to selected materials.

1 Claim, 9 Drawing Sheets

```
SEQ ID NO:1:     1 ATG GAA ACG GAA AGG GAG GAA AAT GTT GTA TAT GGC CCT CTG CCA TTC TAC CCC ATT GAA
SEQ ID NO:2:     1  M   E   T   E   R   E   E   N   V   V   Y   G   P   L   P   F   Y   P   I   E
                61 GAA GGA TCA GCT GGA ATT CAG CTT ACT TTG CAT GGA GTG AAG TAC AAA GCC TAT GGA GCA
                21  E   G   S   A   G   I   Q   L   T   L   H   G   V   K   Y   K   A   Y   G   A
               121 ATT GCT AGT TTT AAC GCC CTT ACT GGA GTG GAT ATT TCT CAA GAA CAA CCG TAC GAT ATT
                41  I   A   S   F   N   A   L   T   G   V   D   I   S   Q   E   Q   P   Y   D   I
               181 ACA TGT CGT TTA GCT GAG ATG GCA GAA TAC AAC TAC AAA ATG GGT CTT ATG CAT ATT GCT
                61  T   C   R   L   A   E   M   A   E   Y   N   Y   K   M   G   L   M   H   I   A
               241 TTG TGC AGT GAA AAT TGT GAA GAA TTT TTC ATC CCT GTG CTT GCT CTT AAT CAC AGT TTG GGC
                81  L   C   S   E   N   C   E   E   F   F   I   P   V   L   A   L   N   H   S   L   G
               301 GTA ACT GTC GCA CAA CCA ACT ATT ACA TTG AGA AAA GGC TTA GAT GAA TTA CCT AAA AGT GTG
               101  V   T   V   A   Q   P   T   I   T   L   R   K   G   L   D   E   L   P   K   S   V
               361 ATC AAA AAA ACA GTT ACA TGC ATC AGC ATT GTT AAA AAG CAC CGT GTA GAG GTA ACC CAC CAC
               121  I   K   K   T   V   T   C   I   S   I   V   K   K   H   R   V   E   V   T   H   H
               421 CAA AAA ACA GTT ACA TGC ATC AGC ATT GTT AAA AAG CAC CGT GTA GAG GTA ACC CAC CAC
               121  Q   K   T   V   T   C   I   S   I   V   K   K   H   R   V   E   V   T   H   H
               481 GGC GAT TGT GTG GAA GAT ATT GGT TTA CCT AAA GGT GGA AAC CAA TCA GTT TCA CCT TTA ATG
               161  G   D   C   V   E   D   I   G   L   P   K   G   G   N   Q   S   V   S   P   L   M
               541 AGC TTT GTA CCC GTA CCC ATT GAT GGT TTA CCT AAA GGT GTA GAA ATT GCT GAA CAC ACC ACT
               181  S   F   V   P   V   P   I   D   G   L   P   K   G   V   E   I   A   E   H   T   T
               601 TCT GGC TCT ACT GGT TTA CCT AAA GGT GTA GAA ATT GCT GAA CAC ACC ACT
               201  S   G   S   T   G   L   P   K   G   V   E   I   A   E   H   T   T
               661 TTC TCA CAC GCT TCA CAC GAT CCA CAA AAC CAA CAA GTT TCA CCT TTA ATG
               221  F   S   H   A   S   H   D   P   Q   N   Q   Q   V   S   P   L   M
               721 ACT GTC GTT CCG TTC CAT CAT TTA ATG ATG TTT GAA GAA TTC GAT GAA CTA TTT CTA
               241  T   V   V   P   F   H   H   L   M   M   F   E   E   F   D   E   L   F   L
               781 GGA TAC CGT ATT GTA ATG TTA ACA AAA TTC GAT GAA CTA TTT CTA
               261  G   Y   R   I   V   M   L   T   K   F   D   E   L   F   L
```
FIG. 1A

```
 841 GAT TAT AAG TGT ACC AGT GTT ATT CTT GTA CCA ACG TTA TTT GCT ATT CTC AAC AGG AGT
 281  D   Y   K   C   T   S   V   I   L   V   P   T   L   F   A   I   L   N   R   S
 901 GAA TTG CTC GAT AAG TTC GAT CTA TCT AAT CTA ACT GAA ATT GCT TCT GGT GGA GCT CCT
 301  E   L   L   D   K   F   D   L   S   N   L   T   E   I   A   S   G   G   A   P
 961 TTG GCA AAA GAA ATT GGT GAA GTC GAA ACG GCT GTC AGA AGA TTT AAT ACC CCA GAA CTA CCC CAG
 321  L   A   K   E   I   G   E   V   E   T   A   V   R   R   F   N   T   P   E   Q
1021 GGT TAC GGA TTG ACA GAA AAA ACG ACA GTA TCT GCA TTA TTC TTC GAG ATC GAT CTT GAC ACT
 321  G   Y   G   L   T   E   K   T   T   V   S   A   L   F   F   E   I   D   L   D   T
1081 CCT GGA GCA TCT GGT GTC AAT CGA GAA GCA CGA ACA GAA GAC CAG TAC GGG TAT AAG TTT ATC ATG
 361  P   G   A   S   G   V   N   R   E   A   R   T   E   D   Q   Y   G   Y   K   F   I   M
1141 AAA ACT TTG ACA AAC ATT GGA GAT GTA GTT CAA AGT AAA GGT CTA ACT GTA GTA GTG GAA AGA
 381  K   T   L   T   N   I   G   D   V   V   Q   S   K   G   L   T   V   V   V   E   R
1201 TTA GGC TAC ATC AAA TAC ATC CCA CAT GGG CAA CAA GCC AAG ATG AAG CAA CCA CAG AAC CAC
 401  L   G   Y   I   K   Y   I   P   H   G   Q   Q   A   K   M   K   Q   P   Q   N   H
1261 CAC ACC GGA GAT ATT AAA TAC ATC TTT GAT GTA GTT CAA AGT AAA GGT CTA ACT ATG AAG GAA ATT
 421  H   T   G   D   I   K   Y   I   F   D   V   V   Q   S   K   G   L   T   M   K   E   I
1321 AAA TCA TTA ATC AAA TAC TTT GAT GTA GTT CAA AGT AAA GGT CTA ACT GTT CGT AGA GAA ATT
 441  K   S   L   I   K   Y   F   D   V   V   Q   S   K   G   L   T   V   R   R   E   I
1381 TTG CAA CAT CCA GGG GCT GTA GTT GTA GTC ATG GAA AGG GGC GTT CGT AGA GAA ATT
 461  L   Q   H   P   G   A   V   V   V   V   M   E   R   G   V   R   R   E   I
1441 GAA CTT CCA GGG GCT GTA GTT CAA AGT AAA GGT CTA ACT ATG AAG GAA ATT
 481  E   L   P   G   A   V   V   Q   S   K   G   L   T   M   K   E   I
1501 GTG GAT TAT GTT AAT AGT CAA AAA GGT GTA GTT CAA AGT AAA GGT CTA ACT
 501  V   D   Y   V   N   S   Q   K   G   V   V   Q   S   K   G   L   T
1561 GTG GAT GAA AAA CCA GTA CCT AAA GGT CTA ACT GTT AGA GAA ATT
 521  V   D   E   K   P   V   P   K   G   L   T   V   R   E   I
1621 CTT AAG CCA CAA CAA GCC AAG ATG TAA
 541  L   K   P   Q   Q   A   K   M   *
```

FIG. 1B

Pairwise Comparisons of the *L. Italica* Luciferase Protein
and the Known Beetle Luciferases

| Luciferase | GenBank Assession Number | Percent Similarity to *L. Italica*[a] |
|---|---|---|
| *H. unmunsana* | AF420006 | 95.8 |
| *H. parvula* | L39929 | 95.6 |
| *L. mingrelica* | S61961 | 95.3 |
| *L. lateralis* | U51019 | 81.0 |
| *L. cruciata* | M26194 | 79.6 |
| *L. turkestanicus* | AY742225 | 64.7 |
| *P. pyralis* | M15077 | 64.4 |
| *L. noctiluca* | X89479 | 64.4 |
| *P. rufa* | AF328553 | 62.8 |
| *P. miyako* | L39928 | 62.6 |
| *P. pennsylvanica* | D25416 | 58.6 |
| *P. pennsylvanica* | D25415 | 58.4 |
| *P. pennsylvanica* | U31240 | 51.3 |
| *P. vivianii* | AF139644 | 50.6 |
| *Phengodes sp.* | b | 47.6 |
| *P. termitilluminans* | c | 46.4 |
| *P. plagiophthalamus (YG)* | S29353 | 46.2 |
| *P. plagiophthalamus (GR)* | S29352 | 46.0 |
| *P. hirtus* | AF139645 | 45.6 |
| *P. plagiophthalamus (OR)* | S29355 | 45.5 |
| *P. plagiophthalamus (YE)* | S29354 | 45.5 |

[a] Percent similarity determined by sequence pair distances using the Clustal method of the Lasergene MegAlign software.

[b] Protein sequence of *Phengodes* luciferase obtained from Keith V. Wood, personal communication.

[c] Protein sequence of Pyrearinus termitilluminans determined by Viviani et al., "Cloning and molecular characeterization of the cDNA for the Brazilian larval click-beetle *Pyrearinus termitilluminans* luciferase," Photochem. Photobiol., 70 (1990), pp. 254-260.

FIG.2

Table 1: Bioluminescence Activity of *L. italica* Luciferase Enzymes at pH 7.8

| Enzyme | Bioluminescence Emission[a] $\lambda_{max}$ (nm) | Bandwidth (nm) 20% | Bandwidth (nm) 50% | Relative Enzyme Activity[b] | Thermostability at 37°C[c] (Half-life, hr) | Thermostability at 37°C[c] Yes/No | Mutations[d] |
|---|---|---|---|---|---|---|---|
| 1. LitWT (wild-type) | 566,607 (sh) | 137 | 95 | 100 | No | 0.06 | None |
| 2. Lit-Gly248Ala+Phe252Ser | 563, 600 (sh) | 143 | 98 | 20 | No | nd | Gly248Ala+Phe252Ser |
| 3. LitGF-G-4 | 551 | 123 | 77 | 79 | Yes | nd | Gly216Ala+Thr217Leu+Ser234Ala+Gly248Ala+Phe252Ser |
| 4. LitGF-G-5 | 563, 600 (sh) | 142 | 99 | 82 | Yes | nd | Gly216Ala+Thr217Leu+Ser234Ala+Gly248Ala+Phe252Ser+Glu356Lys |
| 5. LitGF-G-10 | 553 | 119 | 73 | 55 | Yes | nd | Gly216Ala+Thr217Leu+Ser234Ala+Val243Ile+Gly248Ala+Phe252Ser |
| 6. LitSer286Thr | 611 | 114 | 61 | 12 | No | nd | Ser286Thr |
| 7. LitS-2 | 610 | 115 | 61 | 57 | Yes | 2.3 | Gly216Ala+Thr217Leu+Ser234Ala+Ser286Thr+Glu356Lys |
| 8. LitS-S-10 | 612 | 118 | 60 | 62 | Yes | nd | Gly216Ala+Thr217Leu+Ser234Ala+Ser286Thr+Glu356Lys+Lys547Gly+Met548Gly |
| 9. LitS-S-11 | 609 | 114 | 62 | 62 | Yes | nd | Gly216Ala+Thr217Leu+Ser234Ala+Ser286Thr+Glu356Lys+Lys547Gly+Met548Gly |
| 10. LitGF-G-11 | 554 | 130 | 86 | 60 | Yes | 2.0 | Gly216Ala+Thr217Leu+Ser234Ala+Val243Ile+Gly248Ala+Phe252Ser+Glu356Lys+Lys547Gly+Met548Gly | nd = not determined

[a] Bioluminescence emission spectra were measured at pH 7.8. Bandwidths (nm) of emission spectra were measured at 20% and 50% of the intensity at the maximum wavelength. The most intense peak is listed first followed by the emission maximum of the shoulder (sh). [b] Flash height based light activity assays were performed on crude lysates or purified proteins when available. The errors associated with the light assays fall within +/- 10% of the value. [c] Thermostability at 37°C was assessed by visual screening (yes/no). Half lives determined by incubating enzymes at 37°C and assaying activity at various time intervals. [d] Mutations of the *L. italica* gene were verified by DNA sequencing, W.M. Keck Biotechnology Laboratory, Yale University.

FIG. 6

Bioluminescence Emission Spectra of LitWT and variants, pH 7.8 at 25°C and 37°C.

Bioluminescence Emission Spectra of LitWT and variants, pH 7.8 at 25°C and 37°C.

SEQUENCE LISTING

```
<160> NUMBER OF SEQ ID NOS: 17

<210> SEQ ID NO 1
<211> LENGTH: 1647
<212> TYPE: DNA
<213> ORGANISM: L. italica
<220> FEATURE:
<221> NAME/KEY: CDS
<222> LOCATION: (1)...(1644)

<400> SEQUENCE: 1
```

-continued

```
atg gaa acg gaa agg gag gaa aat gtt gta tat ggc cct ctg cca ttc      48
Met Glu Thr Glu Arg Glu Glu Asn Val Val Tyr Gly Pro Leu Pro Phe
 1               5                  10                  15 tac ccc att gaa gaa gga tca gct gga att cag ttg cat aag tac atg      96
Tyr Pro Ile Glu Glu Gly Ser Ala Gly Ile Gln Leu His Lys Tyr Met
             20                  25                  30 caa caa tat gcc aaa ctt gga gca att gct ttt agt aac gcc ctt act     144
Gln Gln Tyr Ala Lys Leu Gly Ala Ile Ala Phe Ser Asn Ala Leu Thr
         35                  40                  45 gga gtg gat att tct tac caa caa tac ttt gat att aca tgt cgt tta     192
Gly Val Asp Ile Ser Tyr Gln Gln Tyr Phe Asp Ile Thr Cys Arg Leu
     50                  55                  60 gct gag gca atg aaa aac tac ggt atg aaa ccg gaa gga cat att gct     240
Ala Glu Ala Met Lys Asn Tyr Gly Met Lys Pro Glu Gly His Ile Ala
 65                  70                  75                  80 ttg tgc agt gaa aat tgt gaa gaa ttt ttc atc cct gtg ctt gct ggt     288
Leu Cys Ser Glu Asn Cys Glu Glu Phe Phe Ile Pro Val Leu Ala Gly
                 85                  90                  95 ctt tac att gga gta act gtc gca cct act aat gaa att tac aca ttg     336
Leu Tyr Ile Gly Val Thr Val Ala Pro Thr Asn Glu Ile Tyr Thr Leu
            100                 105                 110 cgt gaa ctt aat cac agt ttg ggc atc gca caa cca act att gta ttc     384
Arg Glu Leu Asn His Ser Leu Gly Ile Ala Gln Pro Thr Ile Val Phe
        115                 120                 125 agc tcc aga aaa ggc tta cct aaa gtt tta gaa gtg caa aaa aca gtt     432
Ser Ser Arg Lys Gly Leu Pro Lys Val Leu Glu Val Gln Lys Thr Val
    130                 135                 140 aca tgc atc aaa aca att gtt att tta gat agt aaa gta aac ttt gga     480
Thr Cys Ile Lys Thr Ile Val Ile Leu Asp Ser Lys Val Asn Phe Gly
145                 150                 155                 160 ggc tac gat tgt gtg gaa act ttt att aag aaa cat gta gaa tta ggt     528
Gly Tyr Asp Cys Val Glu Thr Phe Ile Lys Lys His Val Glu Leu Gly
                165                 170                 175 ttt cca gca act agc ttt gta ccc att gat gta aag gac cgt aaa cat     576
Phe Pro Ala Thr Ser Phe Val Pro Ile Asp Val Lys Asp Arg Lys His
            180                 185                 190 cac att gct ttg ctt atg aat tct tct ggc tct act ggt tta cct aaa     624
His Ile Ala Leu Leu Met Asn Ser Ser Gly Ser Thr Gly Leu Pro Lys
        195                 200                 205 ggt gta gag att acc cac gaa gga aca gtt aca aga ttc tca cac gct     672
Gly Val Glu Ile Thr His Glu Gly Thr Val Thr Arg Phe Ser His Ala
    210                 215                 220 aag gat cca att tac gga aac caa gtt tca cct ggt act gct att tta     720
Lys Asp Pro Ile Tyr Gly Asn Gln Val Ser Pro Gly Thr Ala Ile Leu
225                 230                 235                 240 act gtc gtt ccg ttc cat cat gga ttt gga atg ttt acc act tta gga     768
Thr Val Val Pro Phe His His Gly Phe Gly Met Phe Thr Thr Leu Gly
                245                 250                 255 tac ttt gct tgt gga tac cgt att gta atg tta aca aaa ttc gat gaa     816
Tyr Phe Ala Cys Gly Tyr Arg Ile Val Met Leu Thr Lys Phe Asp Glu
            260                 265                 270 gaa cta ttt ttg aga act ttg caa gat tat aag tgt acc agt gtt att     864
Glu Leu Phe Leu Arg Thr Leu Gln Asp Tyr Lys Cys Thr Ser Val Ile
        275                 280                 285 ctt gta cca acg tta ttt gct att ctc aac agg agt gaa ttg ctc gat     912
Leu Val Pro Thr Leu Phe Ala Ile Leu Asn Arg Ser Glu Leu Leu Asp
    290                 295                 300 aag ttc gat tta tct aat cta act gaa att gct tct ggt gga gct cct     960
Lys Phe Asp Leu Ser Asn Leu Thr Glu Ile Ala Ser Gly Gly Ala Pro
```

-continued

| | | |
|---|---|---|
| ttg gca aaa gaa att ggt gaa gca gtc gct aga aga ttt aat cta ccc<br>Leu Ala Lys Glu Ile Gly Glu Ala Val Ala Arg Arg Phe Asn Leu Pro<br>                325                          330                    335 | 1008 |
| ggt gtc cgt cag ggt tac gga ttg aca gaa acg aca tct gca ttt att<br>Gly Val Arg Gln Gly Tyr Gly Leu Thr Glu Thr Thr Ser Ala Phe Ile<br>         340                    345                        350 | 1056 |
| att acc cca gaa ggt gat gat aaa cct gga gca tct gga aaa gta gta<br>Ile Thr Pro Glu Gly Asp Asp Lys Pro Gly Ala Ser Gly Lys Val Val<br>355                        360                        365 | 1104 |
| ccc tta ttc aaa gta aaa att att gat ctt gac act aaa aaa act ttg<br>Pro Leu Phe Lys Val Lys Ile Ile Asp Leu Asp Thr Lys Lys Thr Leu<br>370                        375                        380 | 1152 |
| ggt gtc aac cga cga gga gag atc tgt gta aaa ggt ccg agt ctt atg<br>Gly Val Asn Arg Arg Gly Glu Ile Cys Val Lys Gly Pro Ser Leu Met<br>385                        390                        395                    400 | 1200 |
| tta ggc tac aca aac aat ccg gaa gca aca aga gaa act att gat gaa<br>Leu Gly Tyr Thr Asn Asn Pro Glu Ala Thr Arg Glu Thr Ile Asp Glu<br>                      405                        410                    415 | 1248 |
| gag ggt tgg ttg cac acc gga gat att gga tat tac gac gaa gac gaa<br>Glu Gly Trp Leu His Thr Gly Asp Ile Gly Tyr Tyr Asp Glu Asp Glu<br>         420                    425                        430 | 1296 |
| cat ttc ttc att gta gat cgt ttg aaa tca tta atc aaa tac aag ggg<br>His Phe Phe Ile Val Asp Arg Leu Lys Ser Leu Ile Lys Tyr Lys Gly<br>                      435                        440                    445 | 1344 |
| tac cag gta cca cct gct gaa ttg gaa tcc gtt ctt ttg caa cat cca<br>Tyr Gln Val Pro Pro Ala Glu Leu Glu Ser Val Leu Leu Gln His Pro<br>450                        455                        460 | 1392 |
| aat atc ttt gat gct ggt gtg gct ggt gtc ccc gat tct gaa gct ggt<br>Asn Ile Phe Asp Ala Gly Val Ala Gly Val Pro Asp Ser Glu Ala Gly<br>465                        470                        475                    480 | 1440 |
| gaa ctt cca ggg gct gta gtt gta atg gaa aaa gga aaa act atg act<br>Glu Leu Pro Gly Ala Val Val Val Met Glu Lys Gly Lys Thr Met Thr<br>                      485                        490                    495 | 1488 |
| gaa aag gaa att gtg gat tat gtt aat agt caa gta gtg aac cac aaa<br>Glu Lys Glu Ile Val Asp Tyr Val Asn Ser Gln Val Val Asn His Lys<br>         500                    505                        510 | 1536 |
| cgt ctg cgt ggt ggc gtt cgt ttt gtg gat gaa gta cct aaa ggt cta<br>Arg Leu Arg Gly Gly Val Arg Phe Val Asp Glu Val Pro Lys Gly Leu<br>                515                    520                        525 | 1584 |
| act ggt aaa att gat gct aaa gta att aga gaa att ctt aag aaa cca<br>Thr Gly Lys Ile Asp Ala Lys Val Ile Arg Glu Ile Leu Lys Lys Pro<br>530                        535                        540 | 1632 |
| caa gcc aag atg taa<br>Gln Ala Lys Met<br>545 | 1647 |

<210> SEQ ID NO 2
<211> LENGTH: 548
<212> TYPE: PRT
<213> ORGANISM: L. italica

<400> SEQUENCE: 2

Met Glu Thr Glu Arg Glu Glu Asn Val Val Tyr Gly Pro Leu Pro Phe
1                        5                          10                        15

Tyr Pro Ile Glu Glu Gly Ser Ala Gly Ile Gln Leu His Lys Tyr Met
                    20                        25                        30

Gln Gln Tyr Ala Lys Leu Gly Ala Ile Ala Phe Ser Asn Ala Leu Thr
                    35                        40                        45

```
Gly Val Asp Ile Ser Tyr Gln Gln Tyr Phe Asp Ile Thr Cys Arg Leu
     50              55                  60

Ala Glu Ala Met Lys Asn Tyr Gly Met Lys Pro Glu Gly His Ile Ala
65              70                  75                  80

Leu Cys Ser Glu Asn Cys Glu Glu Phe Phe Ile Pro Val Leu Ala Gly
                85                  90                  95

Leu Tyr Ile Gly Val Thr Val Ala Pro Thr Asn Glu Ile Tyr Thr Leu
            100                 105                 110

Arg Glu Leu Asn His Ser Leu Gly Ile Ala Gln Pro Thr Ile Val Phe
        115                 120                 125

Ser Ser Arg Lys Gly Leu Pro Lys Val Leu Glu Val Gln Lys Thr Val
    130                 135                 140

Thr Cys Ile Lys Thr Ile Val Ile Leu Asp Ser Lys Val Asn Phe Gly
145                 150                 155                 160

Gly Tyr Asp Cys Val Glu Thr Phe Ile Lys Lys His Val Glu Leu Gly
            165                 170                 175

Phe Pro Ala Thr Ser Phe Val Pro Ile Asp Val Lys Asp Arg Lys His
        180                 185                 190

His Ile Ala Leu Leu Met Asn Ser Ser Gly Ser Thr Gly Leu Pro Lys
    195                 200                 205

Gly Val Glu Ile Thr His Glu Gly Thr Val Thr Arg Phe Ser His Ala
210                 215                 220

Lys Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
            245                 250                 255

Tyr Phe Ala Cys Gly Tyr Arg Ile Val Met Leu Thr Lys Phe Asp Glu
        260                 265                 270

Glu Leu Phe Leu Arg Thr Leu Gln Asp Tyr Lys Cys Thr Ser Val Ile
    275                 280                 285

Leu Val Pro Thr Leu Phe Ala Ile Leu Asn Arg Ser Glu Leu Leu Asp
290                 295                 300

Lys Phe Asp Leu Ser Asn Leu Thr Glu Ile Ala Ser Gly Gly Ala Pro
305                 310                 315                 320

Leu Ala Lys Glu Ile Gly Glu Ala Val Ala Arg Arg Phe Asn Leu Pro
            325                 330                 335

Gly Val Arg Gln Gly Tyr Gly Leu Thr Glu Thr Thr Ser Ala Phe Ile
        340                 345                 350

Ile Thr Pro Glu Gly Asp Asp Lys Pro Gly Ala Ser Gly Lys Val Val
    355                 360                 365

Pro Leu Phe Lys Val Lys Ile Ile Asp Leu Asp Thr Lys Lys Thr Leu
370                 375                 380

Gly Val Asn Arg Arg Gly Glu Ile Cys Val Lys Gly Pro Ser Leu Met
385                 390                 395                 400

Leu Gly Tyr Thr Asn Asn Pro Glu Ala Thr Arg Glu Thr Ile Asp Glu
            405                 410                 415

Glu Gly Trp Leu His Thr Gly Asp Ile Gly Tyr Tyr Asp Glu Asp Glu
        420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Ser Glu Ala Gly
```

-continued

```
            465                 470                 475                 480
Glu Leu Pro Gly Ala Val Val Met Glu Lys Gly Lys Thr Met Thr
                    485                 490                 495

Glu Lys Glu Ile Val Asp Tyr Val Asn Ser Gln Val Val Asn His Lys
                500                 505                 510

Arg Leu Arg Gly Gly Val Arg Phe Val Asp Glu Val Pro Lys Gly Leu
            515                 520                 525

Thr Gly Lys Ile Asp Ala Lys Val Ile Arg Glu Ile Leu Lys Lys Pro
        530                 535                 540

Gln Ala Lys Met
545

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer sequence

<400> SEQUENCE: 3
gtccctaaac ggtagaggaa aag                                              23

<210> SEQ ID NO 4
<211> LENGTH: 25
<212> TYPE: DNA
<213> ORGANISM: Artificial Sequence
<220> FEATURE:
<223> OTHER INFORMATION: Synthetic Primer sequence

<400> SEQUENCE: 4
gtcttcttat gagtagttta gttac                                            25

<210> SEQ ID NO 5
<211> LENGTH: 27
<212> TYPE: DNA
<213> ORGANISM: Artificial Sequence
<220> FEATURE:
<223> OTHER INFORMATION: Synthetic Primer sequence

<400> SEQUENCE: 5
tttaatcccg gggtccctaa acggtag                                          27

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer sequence

<400> SEQUENCE: 6
ctaagcctcg agtcttctta tgagtagtt                                        29

<210> SEQ ID NO 7
<211> LENGTH: 43
<212> TYPE: DNA
<213> ORGANISM: Artificial Sequence
<220> FEATURE:
<223> OTHER INFORMATION: Synthetic Primer sequence

<400> SEQUENCE: 7
gattctcaca cgctaaggac ccaatttacg gaaaccaagt ttc                        43

<210> SEQ ID NO 8
```

```
<211> LENGTH: 42
<212> TYPE: DNA
<213> ORGANISM: Artificial Sequence
<220> FEATURE:
<223> OTHER INFORMATION: Synthetic Primer sequence

<400> SEQUENCE: 8
cggtagagga aaagtttgga tccatggaaa cggaaaggga gg                          42

<210> SEQ ID NO 9
<211> LENGTH: 44
<212> TYPE: DNA
<213> ORGANISM: Artificial Sequence
<220> FEATURE:
<223> OTHER INFORMATION: Synthetic Primer sequence

<400> SEQUENCE: 9
gattataagt gtaccactgt tattctggta ccaacgttat ttgc                        44

<210> SEQ ID NO 10
<211> LENGTH: 42
<212> TYPE: DNA
<213> ORGANISM: Artificial Sequence
<220> FEATURE:
<223> OTHER INFORMATION: Synthetic Primer sequence

<400> SEQUENCE: 10
ccgttccatc acgcgtttgg aatgtctacc actttaggat ac                          42

<210> SEQ ID NO 11
<211> LENGTH: 36
<212> TYPE: DNA
<213> ORGANISM: Artificial Sequence
<220> FEATURE:
<223> OTHER INFORMATION: Synthetic Primer sequence

<400> SEQUENCE: 11
agaaaccaca agccgggggg taaatcggtc aaaatg                                 36

<210> SEQ ID NO 12
<211> LENGTH: 38
<212> TYPE: DNA
<213> ORGANISM: Artificial Sequence
<220> FEATURE:
<223> OTHER INFORMATION: Synthetic Primer sequence

<400> SEQUENCE: 12
gcatttatta ttaccccaaa aggtgatgat aaacctgg                               38

<210> SEQ ID NO 13
<211> LENGTH: 36
<212> TYPE: DNA
<213> ORGANISM: Artificial Sequence
<220> FEATURE:
<223> OTHER INFORMATION: Synthetic Primer sequence

<400> SEQUENCE: 13
agaaaccaca agccgggggg taaatcggtc aaaatg                                 36

<210> SEQ ID NO 14
<211> LENGTH: 38
<212> TYPE: DNA
<213> ORGANISM: Artificial Sequence
<220> FEATURE:
<223> OTHER INFORMATION: Synthetic Primer sequence

<400> SEQUENCE: 14
```

```
-continued gcatttatta ttaccccaaa aggtgatgat aaacctgg                              38

<210> SEQ ID NO 15
<211> LENGTH: 40
<212> TYPE: DNA
<213> ORGANISM: Artificial Sequence
<220> FEATURE:
<223> OTHER INFORMATION: Synthetic Primer sequence

<400> SEQUENCE: 15
gagattaccc acgaagcact agttacaaga ttctcacacg                            40

<210> SEQ ID NO 16
<211> LENGTH: 29
<212> TYPE: DNA
<213> ORGANISM: Artificial Sequence
<220> FEATURE:
<223> OTHER INFORMATION: Synthetic Primer sequence

<400> SEQUENCE: 16
tacggaaacc aagttgcacc tggtactgc                                        29

<210> SEQ ID NO 17
<211> LENGTH: 35
<212> TYPE: DNA
<213> ORGANISM: Artificial Sequence
<220> FEATURE:
<223> OTHER INFORMATION: Synthetic Primer sequence

<400> SEQUENCE: 17
taactgtcat tccgttccat cacgcgtttg gaatg                                 35
```

ISOLATED LUCIFERASE GENE OF L. ITALICA

CROSS REFERENCE TO RELATED APPLICATIONS

This application claims priority to U.S. Provisional Patent Application No. 60/772,804, filed on Feb. 13, 2006, the entirety of which is incorporated by reference herein.

STATEMENT OF GOVERNMENT SUPPORT

This invention was made in part with government support under grant number MCB-0444577 from the National Science Foundation and FA9550-04-1-0211 from the Air Force Office of Scientific Research. The government has certain rights in this invention.

BACKGROUND OF THE INVENTION

1. Field of the Invention

The present invention relates to a luciferase gene, polypeptide, and mutants thereof. More particularly, the present invention relates to a luciferase gene, polypeptide, and mutants thereof from the firefly *Luciola italica*.

2. Brief Description of Art

Bioluminescence is the emission of light from an organic molecule, such as luciferin, which has been oxidized by oxygen or one of its metabolites. The reaction is catalyzed by the luciferase protein (Luc), a naturally occurring protein that is found in beetles, fireflies and other living organisms, to form luciferyl-adenylate ($LH_2$-AMP) from substrates luciferin ($LH_2$) and ATP (eq. 1). Through a multi-step oxidative process, $LH_2$-AMP is converted to excited state oxyluciferin, the light-emitting product (eq. 2-3) (H. H. Seliger et al., Arch. Biochem. Biophys. 88 (1960) 136-141; E. H. White et al., Bioorg. Chem. 1 (1971) 92-122; M. DeLuca; Adv. Enzymol. 44 (1976) 37-68; J.-Y. Koo et al., Proc. Natl. Acad. Sci. USA 75 (1978) 30-33; J. W. Hastings; Bioluminescence, in: Sperelakis, N., (Ed.), Cell Physiology Source Book, Academic Press, New York, 1995, pp. 665-681; K. V. Wood; Photochem. Photobiol. 62 (1995) 662-673).

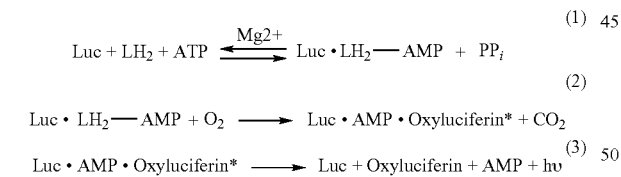

$$\text{Luc} + LH_2 + ATP \xrightleftharpoons{Mg^{2+}} \text{Luc} \cdot LH_2 - AMP + PP_i \quad (1)$$

$$\text{Luc} \cdot LH_2 - AMP + O_2 \longrightarrow \text{Luc} \cdot AMP \cdot \text{Oxyluciferin}^* + CO_2 \quad (2)$$

$$\text{Luc} \cdot AMP \cdot \text{Oxyluciferin}^* \longrightarrow \text{Luc} + \text{Oxyluciferin} + AMP + h\upsilon \quad (3)$$

The generation of light from $LH_2$ is highly efficient (Seliger et al., supra) affording great sensitivity for the detection of the luciferase protein using available light measuring technology. Thus, the luciferase gene is extremely suitable for reporter gene applications (S. J. Gould et al., Anal. Biochem. 175 (1988) 5-13) and in vivo bioluminescence imaging (C. H. Contag et al., Annu. Rev. Biomed. Eng. 4 (2002) 235-260). Luciferases have been used to study gene delivery (Y. Taniyama et al., Gene Ther. 9 (2002) 372-380), gene silencing (P. J. Paddison et al., Proc. Natl. Acad. Sci. USA 99 (2002) 1443-1448) and real-time imaging of luciferase expression in live animals (L. F. Greer, III, et al., Luminescence 17 (2002) 43-74).

Currently, luciferase genes from various species, including *Photinus pyralis* (common North American firefly), *Pyrophorus plagiophathalamus* (Jamaican click beetle), *Luciola mingrelica* (European beetle), and *Lampyris noctiluca* (glow worm), are used to generate luminescent reporter moieties.

Typically, these reporter moieties emit light in the blue to yellow-green range (400-560 nm) or the green to orange range (510-590 nm). However, emission of light at other wavelengths is useful in many applications. For example, light emitted at a wavelength closer to the red range ("red shifted") is known to be transmitted through live tissue more efficiently than other wavelengths of visible light. Similarly, light emitted at a wavelength closer to the blue range ("blue shifted") provides increased sensitivity to standard photomultiplier tubes and is important for dual color assays where it is important to maximize the wavelength separation of the signals. By shifting the bioluminescence emission toward the red or blue wavelengths, it is possible to enhance the utility of luciferase genes in in vivo monitoring and gene expression assays.

There are many uses of luciferase known in the art. Luciferase, from various sources, has been used in various assays and reporting capacities. For example, U.S. Pat. No. 6,387,675 discloses the use of the luciferase gene of the elaterid beetle, *P. plagiophthalamus*, in eukaryotic cells for biosensing. U.S. Pat. No. 6,812,012 discloses a method of using luciferase to assay intracellular ATP, while a method of using a luciferase gene as a reporter gene is disclosed in U.S. Pat. No. 6,495,355.

Expression of luciferase genes has also been shown in the art. For example, U.S. Pat. No. 6,132,983 discloses the expression of luciferase genes in cells of various host organisms, while U.S. Pat. No. 4,968,613 discloses production of luciferase by incorporating a luciferase gene into a vector inserted into *E. coli*. U.S. Pat. No. 5,229,285 discloses the expression of a thermostable luciferase of a firefly.

Alteration of the bioluminescence emission of currently used luciferases can be obtained by amino acid substitutions and other mutations in the active sites of the luciferase genes. Although a number of such luciferases are available commercially, additional luciferase derivatives with altered spectral properties would be desirable.

SUMMARY OF THE INVENTION

In one aspect, the present invention is directed to an isolated polypeptide comprising the sequence of SEQ ID NO:2, wherein said polypeptide produces a bioluminescence emission maximum of approximately 566 nm. Specific mutations of the polypeptide of SEQ ID NO:2 are also encompassed in the claimed invention, as well as the nucleic acid sequences that correspond to the polypeptide of SEQ ID NO:2 and the specific mutants thereof.

In another aspect, the present invention is directed to a cell transformed with a vector containing one of the aforementioned nucleic acid sequences.

In another aspect, the present invention is directed to a method for detecting the presence of a *L. italica* luciferase in a cell, the method comprising: introducing one of the aforementioned vectors into the cell; contacting said cell with a luciferase substrate; and detecting a bioluminescence emission at a wavelength between about 551 to about 612 nm.

In another aspect, the present invention is directed to a method for assaying the presence of ATP in a sample, the method comprising the steps of: combining a sample with one of the aforementioned polypeptides; measuring a bioluminescence emission of said sample at a selected wavelength that corresponds to a bioluminescence emission max of said isolated polypeptide; and correlating said bioluminescence emission max with the presence of ATP.

In another aspect, the present invention is directed to an article of manufacture comprising a container containing any of the isolated polypeptides described above.

These and other aspects will become apparent upon reading the following detailed description of the invention.

BRIEF DESCRIPTION OF THE DRAWINGS

The invention will be more fully understood from the following detailed description taken in conjunction with the accompanying drawings in which:

FIG. 1 shows a nucleic acid sequence of the Italian firefly, *L. italica* (SEQ ID NO: 1) and the translated polypeptide sequence (SEQ ID NO: 2);

FIG. 2 shows a table comparing the *L. italica* luciferase protein to the known beetle luciferases;

FIG. 6 shows bioluminescence activity of Lit WT and mutants thereof;

DETAILED DESCRIPTION OF THE INVENTION

Isolated nucleic acid and polypeptide compositions encoding a *L. italica* firefly luciferase are disclosed herein, as well as mutants of these isolated nucleic acid and polypeptide sequences. It has been found that the wild type *L. italica* (Lit WT) luciferase has a bioluminescence emission maximum that is red-shifted and 566 nm with a shoulder at 607 nm. Further, various substitution mutants of Lit WT exhibit distinct emission spectra that are red- or blue-shifted depending on the specific mutation(s). As defined herein, the term "red-shifted" means that the bioluminescence emission has been shifted toward the red wavelength range as compared to other luciferases known in the art. Similarly, "blue-shifted" means that the bioluminescence emission has been shifted toward the blue wavelength range as compared to other luciferases known in the art.

Lit WT is encoded by a nucleic acid having a sequence of SEQ. ID. NO.: 1 as shown in FIG. 1. The nucleic acid of SEQ ID NO: 1 was isolated from the Italian firefly, *L. italica* and is available in GenBank at Accession No. DQ138966. After isolation of SEQ ID NO: 1, the nucleic acid was amplified by amplification techniques known in the art, such as PCR. The nucleic acid was then inserted into an appropriate vector, such as a pGEX-6p-2 plasmid, and transformed into competent cells and subsequently plated. DNA sequencing revealed a 1647 bp open reading frame corresponding to a polypeptide containing 548 amino acids, having a sequence of SEQ ID NO: 2, also shown in FIG. 1. The Lit WT protein was found to have a molecular mass of 60,908±6 Da, as determined by electrospray ionization mass spectrometry. This value corresponds to the calculated mass of 60,907±6 Da of Lit WT, which contains the additional N-terminal peptide GlyPro-LeuGlySer-.

As shown in FIG. 2, SEQ ID NO:2 is highly homologous to other luciferase amino acid sequences, including *H. unmunsana* (95.8%), *H. parvula* (95.6%) and *L. mingrelica* (95.3%). The luciferases least homologous to *L. italica* were the orange and yellow emitting isozymes of the click beetle *P. plagiophthalamis* (45.5%). Generally higher homology to the *L. italica* luciferase was found with true fireflies. The homologies were determined by sequence pair distances using the Clustal V method (Higgins et al., Computer Applications in the Biosciences, vol. 5, p. 151-153 (1989)).

Figure 3:
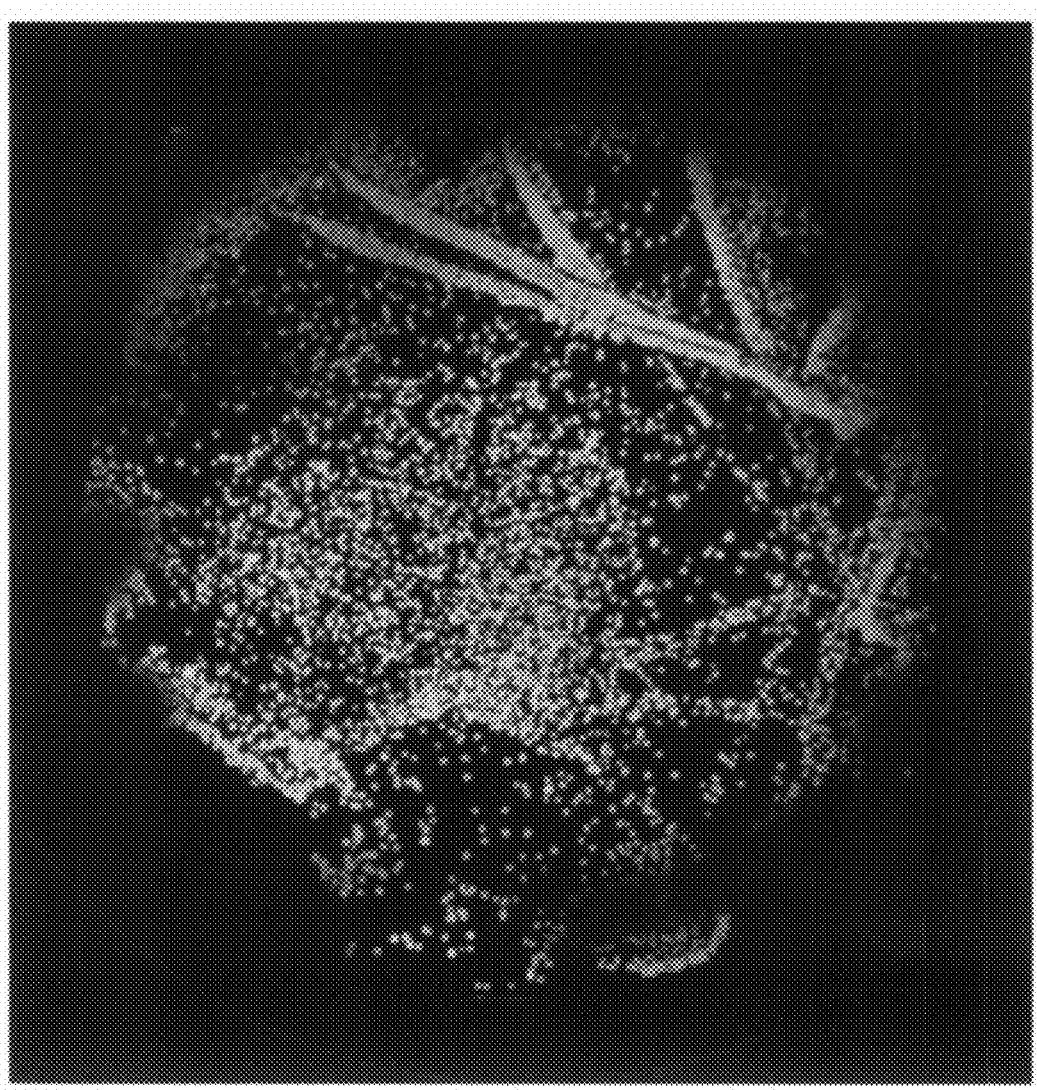
FIG. 3 shows glowing colonies of *E. coli* infused with luciferin on nitrocellulose filters.

To analyze the bioluminescence emission of *L. Italica* luciferase, proteins were expressed as a GST-fusion protein in bacterial colonies. Expression of the luciferase was demonstrated by the observation of bioluminescent colonies of *E. coli* infused with a luciferase substrate, such as luciferin, on nitrocellulose fibers as shown in FIG. 3. The bioluminescence emission of Lit WT was measured, using methods known in the art, and determined to be approximately 566 nm with a shoulder at 607 nm.

Figure 4:
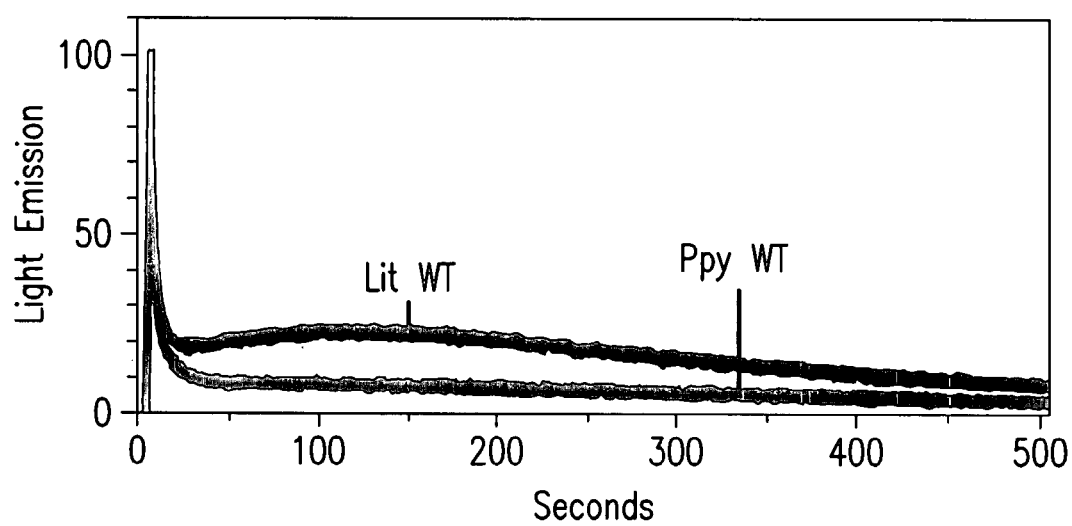
FIG. 4 shows decay of bioluminescence emission of Lit WT and Ppy WT luciferases.

Preliminary characterization showed that Lit WT demonstrates bioluminescence emission similar in intensity to *P. pyralis* (Ppy WT). Specifically, it was determined that the relative flash height specific activity of Lit WT, which relates to the maximum achievable overall reaction rate, was found to be approximately 95% of that of Ppy WT. However, compared to Ppy WT, Lit WT has an extended light emission decay and is red-shifted by 9 nm. As shown in FIG. 4, Ppy WT and Lit WT decay to approximately 20% of their maximum flash height in about 0.2 minutes. Ppy WT continues to rapidly decay and reaches 10% of its initial activity in about 0.35 minute. In contrast, Lit WT reaches 10% of its flash height at about 7 minutes, illustrating its extended light emission decay.

Figure 5A:
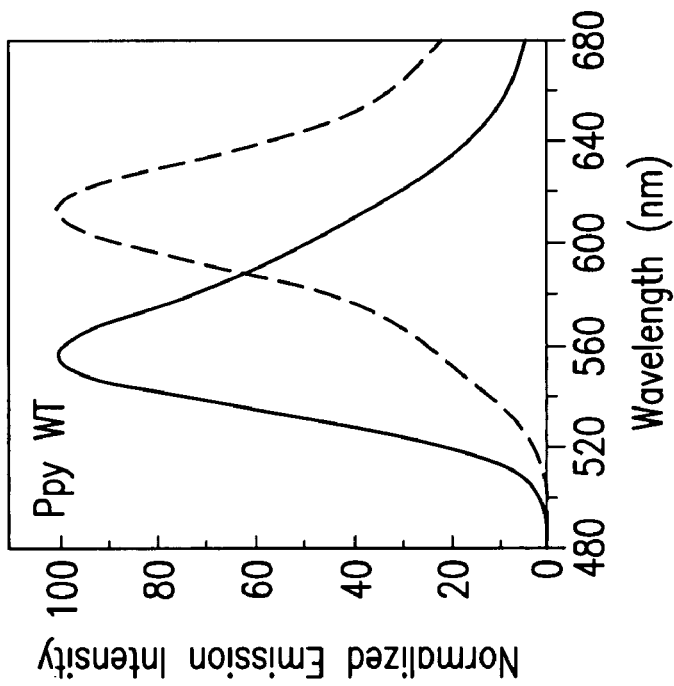
FIG. 5 shows bioluminescence emission spectra for *L. italica* (Panel A) and *P. pyralis* (Panel B)
Figure 5B:
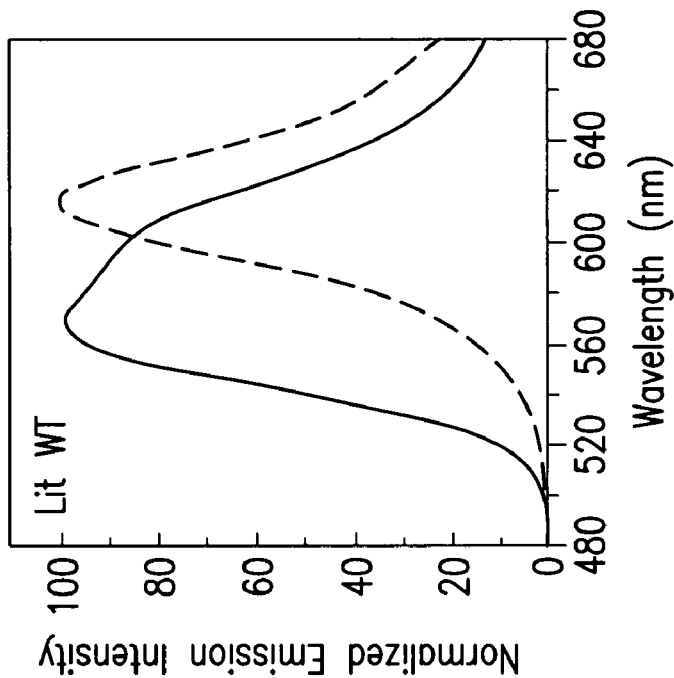

In addition to its extended bioluminescence emission decay as compared to other luciferases, the Lit WT has been red-shifted. As shown in FIG. 5, bioluminescence emission spectra at pH 7.8 showed an emission maximum of 566 nm with a shoulder at 607 nm for Lit WT (FIG. 5, Panel A). This represents a 9 nm shift from Ppy WT, which has an emission maximum of 557 nm (FIG. 5, Panel B). At a pH of 6.0, Lit WT was found to be very sensitive, shifting to 614 nm, thereby producing a spectrum very similar to Ppy WT at this pH.

Further, it has also been found that mutants of Lit WT produce bioluminescence emissions that are red-shifted or blue-shifted, and have extended bioluminescence emission decay. As shown in FIG. 6, substitutions of various amino acids in Lit WT result in bioluminescence emissions of different wavelengths. In addition, as shown in FIG. 6, several of the disclosed mutants display excellent thermostability at 37° C., a property of great importance for many applications, including but not limited to in vivo imaging of tumors, biosensor applications, reporter gene applications in mammalian cell lines, and the like. As shown in FIG. 6, the half-lives of LitWT, LitS-S-2 and LitGF-G-11 were measured. In the first mutant, Lit-Gly 248 Ala+Phe 252Ser, Gly 248 was changed to alanine and Phe 252 was changed to serine. This mutant produced an emission maximum of about 563 nm (a "blue-shift" relative to the emission maximum of 566 nm in Lit WT). This mutant was not thermostable at 37° C., having a half-life of 0.06 hr at this temperature.

In the second mutant, Lit GF-G-4, Gly 216 was changed to alanine, Thr 217 was changed to leucine, Ser 234 was changed to alanine, Gly 248 was changed to alanine and Phe 252 was changed to serine. This mutant has an emission maximum of approximately 551 nm (a blue-shift relative to the emission maximum of 566 nm in Lit WT), and was thermostable at 37° C.

In the third mutant, Lit GF-G-5, Gly 216 was changed to alanine, Thr 217 was changed to leucine, Ser 234 was changed to alanine, Gly 248 was changed to alanine, Phe 252 was changed to serine and Glu 356 was changed to lysine. This mutant has an emission maximum of approximately 563 nm (a blue shift relative to the emission maximum of 566 nm in Lit WT), and was thermostable at 37° C.

In the fourth mutant, Lit GF-G-10, Gly 216 was changed to alanine, Thr 217 was changed to leucine, Ser 234 was changed to alanine, Gly 248 was changed to alanine, Phe 252 was changed to serine, and Val 241 was changed to isoleucine. This mutant had an emission maximum of approximately 553 nm (a blue shift relative to the emission maximum of 566 nm in Lit WT), and was thermostable at 37° C.

In the fifth mutant, Lit-Ser 286 Thr, Ser 286 was changed to threonine. This mutant had an emission maximum of approximately 611 nm (a "red-shift" relative to the emission maximum of 566 nm in Lit WT), but was not thermostable at 37° C.

In the sixth mutant, Lit S-S-2, Gly 216 was changed to alanine, Thr 217 was changed to leucine, Ser 234 was changed to alanine, Ser 286 was changed to threonine and Glu 356 was changed to lysine. This mutant had an emission maximum of approximately 611 nm (a red-shift relative to the emission maximum of 566 nm in Lit WT), and was thermostable at 37° C., having a half-life of 2.3 hours at this temperature compared to 0.06 hr for Lit WT.

In the seventh mutant, Lit S-S-10, Gly 216 was changed to alanine, Thr 217 was changed to leucine, Ser 286 was changed to threonine, and Glu 356 was changed to lysine. This mutant had an emission maximum of approximately 612 nm (a red-shift relative to the emission maximum of 566 nm in Lit WT), and was thermostable at 37° C.

In the eighth mutant, LitS-S-11, Gly 216 was changed to alanine, Thr 217 was changed to leucine, Ser 234 was changed to alanine, Ser 286 was changed to threonine, Glu 356 was changed to lysine, Lys 547 was changed to glycine and Met 548 was changed to glycine. This mutant had an emission maximum of approximately 609 nm (a red-shift relative to the emission maximum of 566 nm in Lit WT), and was thermostable at 37° C. The changes at positions 547 and 548 removed a signal sequence that targets the enzyme for export to the peroxisome.

In the ninth mutant, LitGF-G-11, Gly 216 was changed to alanine, Thr 217 was changed to leucine, Ser 234 was changed to alanine, Val 243 was changed to isoleucine, Gly 248 was changed to alanine, Phe 252 was changed to serine, Glu 356 was changed to lysine, Lys 547 was changed to glycine and Met 548 was changed to glycine. This mutant had an emission maximum of approximately 554 nm (a blue-shift relative to the emission maximum of approximately 566 nm in Lit WT), and was thermostable at 37° C., having a half-life of 2.0 hours at this temperature as compared to 0.06 hr for Lit WT. The changes at positions 547 and 548 removed a signal sequence that targets the enzyme for export to the peroxisome.

Figure 7A:
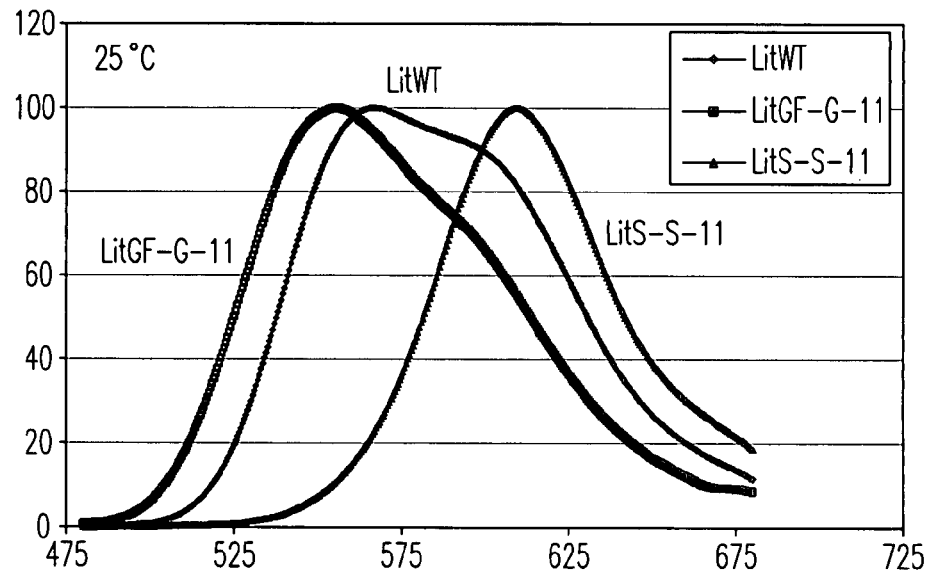
FIG. 7 shows normalized bioluminescence emission spectra produced by luciferases from Lit WT, LitGF-G-10, and LitS-1-11 mutants at 25° C. (Panel 7A) and 37° C. (Panel 7B)
Figure 7B:
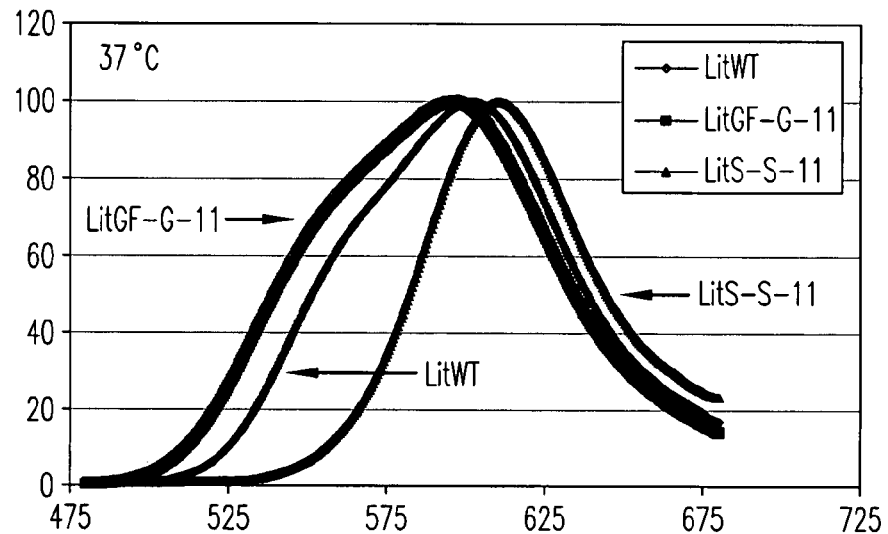

The bioluminescence emission of the Lit GF-G-11 and Lit S-S-11 mutants was compared to the emission of Lit WT. As shown in FIG. 7A, at 25° C., the emission maximum of the LitGF-G-11 mutant was approximately 554, while the LitS-S-11 mutant was approximately 609 nm, thus demonstrating the blue- and red-shifts shown with these mutants relative to Lit WT. As shown in FIG. 7B, at 37° C., all the spectra are red-shifted. It is noted that the red-shifting of red emitting luciferases is favorable for in vivo imaging.

The mutants of Lit WT as shown in FIG. 6 and described in more detail above were made through processes known in the art, such as site directed mutagenesis and multi-site directed mutagenesis. These processes are discussed in more detail in the Examples that follow.

Further modifications and changes beyond those specifically disclosed herein may be made to the nucleic acid sequence or polypeptide sequence of the L. italica luciferase to obtain a molecule having the desired bioluminescence emission and extended light decay. For example, certain amino acids may be substituted for other amino acids without any loss of function. So long as the mutation or change maintains a red-shifted luciferase, the resulting protein will be considered a biologically functional equivalent for the purposes of the present invention.

Additionally, the nucleic acid sequence of Lit WT may be modified chemically or by genetic engineering to enable the luciferase to be targeted into a specific subcellular compartment. For example, L. italica luciferase contains the peptide Ala-Lys-Met at the C-terminus, which likely directs the luciferase to the peroxisomes. However, a suitable sequence at the N-terminus will locate the luciferase in the mitochondria while other peptide sequences will direct the luciferase to the endoplasmic reticulum. Direction of the luciferase to certain subcellular compartments may have applicability in different assays and tests known in the art.

Transformation, transduction or transfection of a cell with nucleic acid segments encoding Lit WT or any mutants thereof, can be used to express the luciferase protein in various eukaryotic and prokaryotic cells. The nucleic acid can be inserted into vectors such as bacteriophages, cosmids, or plasmids which can then be used for transformation of prokaryotic or eukaryotic cells according to methods known in the art.

After transforming, transfecting or transducing a host cell with a vector containing Lit WT or a variant thereof, the presence of the L. italica luciferase in a host cell can be determined by contacting the host cell with a luciferase substrate. Luciferase substrates include luciferin and ATP. Through a multi-step oxidative process, the luciferase is converted to an excited state oxyluciferin, which is the bioluminescent product. In the present invention, the bioluminescence emission of the L. italica luciferase is between about 563 nm to about 612 nm. The bioluminescence emission is detected and calculated by processes known to those with ordinary skill in the art.

Alternatively, the luciferase of the present invention may be used to determine the presence and quantify the amount of ATP present in a sample. To do so, a sample that contains, or is thought to contain, ATP is combined with Lit WT or a mutant thereof. The Lit WT or mutant thereof may be in combination with other materials, such as a carrier. Upon contact of the luciferase with the sample, bioluminescence emission is measured to determine whether ATP is present in the sample, and if so, how much ATP is present. Examples of such assays are known in the art (Lundin, A. et al., Meth. Enzymol., Vol. 305, pp. 346-370 (2000), Academic Press, NY; Stanley, P. Journal of Bioluminescence and Chemiluminescence, vol. 4(1), pp. 375-80, (1989); Leach, F., J. Appl. Biochem., vol. 3(6), pp. 473-517 (1989)).

For applicability in assays, tests, methods and techniques known in the art, and those subsequently discovered, the isolated polypeptides of the present invention may be manufactured and place into kits, testing products, or other articles of manufacture. Typically the isolated polypeptides are placed in a container with or without a carrier, such as a buffer. In most instances the article of manufacture contains an instruction booklet.

The wild type and mutant species of the luciferases derived from *L. italica* as disclosed herein are useful in many applications. For example, the present invention is useful in biotechnological applications, including reporter genes, dual-reporter systems, bioluminescence resonance energy transfer (BRET), microarrays, in vivo and ex vivo bioluminescence imaging, tumor research, whole animal imaging, infectious disease monitoring, biosensors for pollutants and biological disease markers, immunoassays, drug development and bioprocessing. (Roda et al., Trends in Biotechnology, vol. 22, No. 6, 295-303, 2004). The present invention is also useful in any application based on the monitoring of ATP levels either directly or through coupled enzyme reactions, such as microbiological tests; assays of enzymes, substrates and cofactors; monitoring of bacterial contamination of food; DNA probes assays; protein blotting and photographic assays (see, for example, L. J. Kricka, Anal. Biochem., vol. 175, pp. 14-21 (1988)). The present invention is also useful in any application based on the emission of light for devices which provide illumination without heat, spark or flame (for example, Cyalume technology). The present invention is also useful in any application in which light emission is used to create a novelty item, e.g. a toy or device that can be worn as jewelry. The present invention is also useful in any materials that could be used in tagging applications or anti-tampering applications.

The thermostable mutant luciferase enzyme of the present invention can also be used as a label for biospecific assays including immunoassays, nucleic acid hybridization both in vitro or microplate plate formats or for imaging purposes (immunohystochemistry or in situ hybridization). The luciferase enzyme of the present invention may possess a histidine tail that may be used for specific coupling with biomolecules, proteins, peptides, nucleic acids and in general organic molecules with suitable reactive groups. The red emitting thermostable luciferase mutant will enhance the performance of assays thanks to its relative high stability up to 42° C. associated with an high turnover of the enzyme and to the possibility to orient the coupling of this enzyme with histidine tail, leaving the acitive site free for substrate access. In addition, different thermostable mutants with different colours can be simultaneously used for multiplexed formats assays in which the reaction is triggered by only one substrate and the signal is selectively recorded at different wavelength.

The following examples are intended to illustrate, but in no way limit the scope of the present invention. All parts and percentages are by weight, and temperatures are in degrees Celsius unless explicitly stated otherwise.

EXAMPLES

Example 1

Isolation of *L. Italica* Luciferase Gene

Collection and RNA Extraction

*L. italica* fireflies were collected from the Bologna-Paderno region of Italy and flash-frozen alive in liquid nitrogen and stored at –80° C. Sixteen lanterns were removed from the fireflies, and were refrozen in liquid nitrogen. The lanterns were ground to a powder using a mortar and pestle cooled with liquid nitrogen. A total of 18 µg of RNA was extracted from the ground lanterns using an RNeasy mini kit (Quiagen) and following the manufacturer's enclosed instructions.

RT-PCR

First strand cDNA synthesis was carried out by utilizing approximately 5 µg of RNA and Oligo (dT) 20 primers and the Superscript TM III First-Strand Synthesis System for RT-PCR (Invitrogen). The following primers based on the luciferase coding sequence of *L. Mingrelica*, were used to amplify the cDNA:

(SEQ ID NO: 3)
5' - GTC CCT AAA CGG TAG AGG AAA A G-3'

(SEQ ID NO: 4)
5' - GTC TTC TTA TGA GTA GTT TAG TTA C-3'

To amplify the cDNA, polymerase chain reaction (PCR) was used. The initial denaturation cycle was at 94° C. for 5 min. A 35 cycle amplification was then carried out at 94° C. for 30 sec.; 52° C. for 45 sec.; and 68° C. for 1.5 min. A final extension was carried out at 68° C. for 5 min.

The PCR products were then analyzed on a 1.0% agarose gel containing ethidium bromide. The samples corresponding to the expected size were purified using a QIA quick PCR purification kit (Qiagen) and following the manufacturer's instructions. Finally, the amplified cDNA was sequenced using a capillary array sequencer CEQ2000XL.

Insertion of cDNA into a Vector

To insert the luciferase cDNA into a vector, a primer set was used to introduce SmaI and XhoI restriction endonuclease sites at the 5' and 3' ends, respectively, of the PCR-amplified cDNA. The following primer set was used:

(SEQ ID NO: 5)
5' - TTT AAT CCC GGG GTC CCT AAA CGG TAG - 3'

(SEQ ID NO: 6)
5' - CTA AGC CTC GAG TCT TCT TAT GAG TAG TT - 3'

PCR amplification and purification were performed as described above.

The PCR product was then digested with SmaI and XhoI restriction endonucleases and ligated into the corresponding cloning sites on a pGEX-6P-2 plasmid. The ligation reaction was transformed into *Escherichia coli* XL-10 Gold ultra competent cells and plated on Luria-Bertani (LB) plates containing 100 µg/mL ampicillin.

Ten colonies of the *E. coli* were selected randomly and plasmid DNA was purified and screened by agarose gel electrophoresis. Several plasmid DNA samples of the expected size were sequenced. One sample containing the entire *L. italica* cDNA was identified.

Alignment of the cDNA Reading Frame

Since the pGEX expression plasmid is designed to produce proteins as N-terminal glutathione-S-transferase (GST)-fusion products, the reading frame of the luciferase gene was realigned so the corresponding protein would contain the same N-terminal polypeptide as Ppy WT. A Quik Change® Site-Directed Mutagenesis kit (Stratagene), was used to realign the reading frame of the *L. italica* cDNA in the pGEX-6P-2 plasmid.

First, the primer, 5'-GA TTC TCA CAC GCT AAG GAC CCA ATT TAC GGA AAC CAA GTT TC-3' (SEQ ID NO:7) and its reverse complement, were used to remove the Bam HI restriction endonuclease site within the *L. italica* luciferase gene. Next, the primer 5'-CG GTA GAG GAA AAG TTT GGA TCC ATG GAA ACG GAA AGG GAG G-3' (SEQ ID NO:8) and its respective reverse complement, were used to introduce a Bam HI site immediately preceding the start codon of the *L. italica* luciferase gene. Finally, the product was digested with Bam HI and XhoI restriction endonucleases and ligated into corresponding cloning sites on the pGEX-6P-2 plasmid.

Expression of *L. Italica* Luciferase as a GST-Fusion Protein in Bacterial Colonies The ligated plasmid DNA was transformed into *E. coli*, which were plated on nitrocellulose filters placed on LB plates containing 100 µg/mL ampicillin. The transformation was done by adding the plasmid DNA to the bacteria at ice temperature, heat shocking the mixture at 42° C., cooling on ice for 2 minutes and recovering for 1 hour at 37° C. in SOC media. The *E. coli* were screened for bioluminescence emission as described in Branchini et al., "Rational and random mutagenesis of firefly luciferase to identify an efficient emitter of red bioluminescence," Proceedings of SPIE, Genetically Engineered and Optical Probes for Biomedical Applications II 5329 (2004), 170-177 (Alexander P. Savitsky et al., eds.).

Colonies having bioluminescence emission were identified by visual screening in a darkroom. Plasmid DNA was isolated and purified therefrom by using a GenElute™ Plasmid Miniprep kit (Sigma), and following the manufacturer's instructions. A single plasmid was selected and the entire *L. italica* luciferase gene was sequenced. The sequence of the *L. italica* luciferase gene in the pGEX plasmid was compared to the sequence obtained from the original cDNA. The comparison showed no differences in the sequence, thereby insuring no additional mutations had been introduced.

Example 2

Preparation of Lit WT Mutants

Nine mutants of Lit WT, shown in FIG. 6 and discussed in more detail above, were prepared using the following methods:

Site Directed Mutagenesis

The Lit-S286T and Lit-G248A and F252S mutants were created by using a QuikChange® Site-Directed Mutagenesis kit (Stratagene). Site-directed mutagenesis was carried out according to the manufacturer's instructions using the *L. italica* wild-type DNA sequence in the pGEX-6P-2 vector as a template. The following primers and their respective reverse complements were used:

```
Lit-S286T:
                                          (SEQ ID NO: 9)
5' - GAT TAT AAG TGT ACC ACT GTT ATT CTG GTA CCA
ACG TTA TTT GC - 3' (Kpn1)

Lit-G248A & F252S:
                                          (SEQ ID NO: 10)
5' - CCG TTC CAT CAC GCG TTT GGA ATG TCT ACC ACT
TTA GGA TAC - 3' (Mlu1)
```

The LitS-S-11 mutant was created by using the QuikChange® Site-Directed Mutagenesis kit (Stratagene). Site-directed mutagenesis was carried out according to the manufacture's instructions using the LitS-S-2 mutant as the template. The 546AlaLysMet548 signal sequence was changed to 546AlaGlyGly548. The following primer and its respective reverse compliment was used to accomplish this:

```
Lys547Gly & Met548Gly:
                                          (SEQ ID NO: 11)
5'- AG AAA CCA CAA GCC GGG GGG TAA ATC GGT CAA
AAT G -3' [BsaB1]
```

The LitGF-G-11 mutant was created by using the QuikChange® Site-Directed Mutagenesis kit (Stratagene). Site-directed mutagenesis was carried out according to the manufacture's instructions using the LitGF-G-10 mutant as the template. First, Glu356Lys was introduced into the template. Once this mutation was confirmed, the 546AlaLysMet548 signal sequence was changed to 546AlaGlyGly548. The following primers and their respective reverse compliments were used to accomplish this:

```
Glu356Lys:
                                          (SEQ ID NO: 12)
5'- GCA TTT ATT ATT ACC CCA AAA GGT GAT GAT AAA
CCT GG -3'

Lys547Gly & Met548Gly:
                                          (SEQ ID NO: 13)
5'- AG AAA CCA CAA GCC GGG GGG TAA ATC GGT CAA
AAT G -3' [BsaB1]
```

Underlining represents silent changes creating a unique screening endonuclease site. Bolded codons represent the mutated codons. Brackets indicate the screening endonuclease.

Multi-Site Directed Mutagenesis

The QuikChange® MultiSite-Directed Mutagenesis kit (Stratagene) was used to create the remaining mutants identified as entries 2 through 8 in FIG. 6. Mutagenesis was carried out according to the manufacturer's instructions for using 1 to 4 primers simultaneously. The Lit-S286T and the Lit-G248A and F252L mutants in the pGEX-6P-2 vector were used as templates with the following primers:

```
Glu356Lys
                                          (SEQ ID NO: 14)
5'- GCA TTT ATT ATT ACC CCA AAA GGT GAT GAT AAA
CCT GG-3'

Gly216Ala & T217L
                                          (SEQ ID NO: 15)
5' - GAG ATT ACC CAC GAA GCA CTA GTT ACA AGA TTC
TCA CAC G - 3'

Ser 234 Ala
                                          (SEQ ID NO: 16)
5' - TAC GGA AAC CAA GTT GCA CCT GGT ACT GC - 3'

Val243Ile
                                          (SEQ ID NO: 17)
5' - TA ACT GTC ATT CCG TTC CAT CAC GCG TTT GGA
ATG - 3'
```

The primer for V243I also includes the G248A mutation (bold and italics) for correct annealing. This primer was only used with the Lit-G248A and F252L template.

Transformation and Screening of Lit WT Mutants

The above-described mutants were transformed into *E. coli* XL-10 Gold ultracompetent cells. Duplicate sets of transformed cells were plated on nitrocellulose filters on LB plates that contained 100 µg/ml ampicillin. The plates were incubated at 37° C. for 18 hrs. Isopropyl B-D-1-thiogalactopyranoside (IPTG) was used to induce transcription.

For each set of transformed mutagenesis product-containing cells, one plate was incubated at room temperature and the other at 37° C. for at least 2 hours. The plates grown at 37° C. were then placed on a plate warmer set to 37° C. (Barnstead Lab Line) and those at room temperature were kept at 22° C.

The nitrocellulose filters were soaked in 1 mM of luciferin in 100 mM NaCitrate buffer (pH 5.5) to induce bioluminescence. Colonies for sequencing were selected on the intensity and color of the emitted light. Plasmid DNA of selected clones was isolated by a standard mini-prep procedure. The DNA was sequenced at Yale University.

Example 3

Protein Purification

Glutathione-S-transferase (GST) fusion constructs of *L. italica* wild-type and mutants thereof selected for sequencing were expressed in XL 10-Gold ultracompetent cells. 7 mL cultures pf the cells were grown in 10 mL culture tubes at 37° C. in LB medium supplemented with 100 µg/mL ampicillin.

These cultures were grown from starter cultures prepared from the picked colonies to mid log phase ($A_{600}$=0.4-0.5) with vigorous shaking, induced with 0.1 mM IPTG, and incubated at 22° C. for 8-10 h. The cells were harvested by centrifugation and placed at −80° C. for no less than 30 min. Cell pellets were resuspended in 0.5 mL of phosphate-buffered saline (PBS), pH 7.3 containing 0.1 mM phenylmethylsulfonyl fluoride (PMSF) and 0.5 mM dithiothreitol (DTT). The resuspended cells were mixed with lysozyme (0.05 volume of 10 mg/mL) and incubated on ice 30 min. The lysated cells were treated with Rnase (10 µg/mL) and Dnase 1 (5 µg/mL). Triton X-100 (2% final volume) was added to the lysate and the whole-cell extract was isolated by centrifugation at 20,000×g for 45 min at 4° C. The supernatant was collected and aliquots were used to determine molecular mass, bioluminescence activity, bioluminescence emission spectra, protein content and GST-activity. Lit WT, LitGF-G-11, LitS-S-2 and LitS-S-11 enzymes were purified to homogeneity as described in Branchini, B. R., et al., "Rational and random mutagenesis of firefly luciferase to identify an efficient emitter of red bioluminescence," Proceedings of SPIE, Genetically Engineered and Optical Probes for Biomedical Applications II, 5329 (2004), 170-177 (Alexander P. Savitsky et al., eds.).

Molecular Mass of Lit WT Protein

The Lit WT protein was found to have a molecular mass of 60 908±6 Da. This value corresponds to the calculated mass of 60 907±6 Da of Lit WT, which contains the additional N-terminal peptide GlyProLeuGlySer-. The mass was determined by Electrospray Ionization Mass Spectrometry.

Glutathione-S-Transferase (GST) Activity Assay to Quantitate GST-Fusion Proteins GST-fusion proteins were quantitated by enzymatic assay of glutathione-S-transferase (GST) activity using the GST substrate 1-chloro-2,4-dinitrobenzene (CDNB). GST catalyzes the conjugation of reduced glutathione (GSH) and CDNB to yield a dinitrophenolthioether, a chromogenic substance with λλmax=340 nm. A dual beam PerkinElmer Lambda 25 UV/Vis spectrophotometer was used to perform these studies.

500 µL of 1 mM reduced glutathione (GSH) and 1 mM 1-chloro-2,4-dinitrobenzene (CDNB) in 0.1M potassium phosphate buffer (KPB), pH 6.5 were placed into 0.7 mL UV transparent sample and reference cuvettes.

50 µL of KPB was added to the reference cuvette. 5 µL of bacterial cell lysate containing the GST-luciferase fusion protein and 45 µL of KPB was added to the sample cuvette. The samples were well mixed and the absorbance at 340 nm was monitored using the Time Drive program of the Lambda 25 spectrophotometer. Data was recorded for 4 min, and the velocity of the reaction, the rate of change in absorbance per minute, was determined. The concentration of GST-fusion protein is proportional to the velocity of the reaction.

Bioluminescence Emission Spectra of Partially Purified Proteins

Bioluminescence emission spectra were obtained using a PerkinElmer LS55 luminescence spectrometer operated in the "bioluminescence" mode. Data was collected over the wavelength range 480-680 nm in a 1 mL optical glass cuvette. Gate and delay times, detector voltage, scan rate, and slit width were adjusted to optimize instrument response. Reaction mixtures containing partially purified *L. italica* wild type and its mutants (0.005 mL) in luciferin and Mg-ATP were brought to a final volume of 0.5 mL with 25 mM glycylglycine, pH 7.8. The spectral data reported in FIG. 6 were measured with purified proteins from Lit WT, LitGF-G-11, LitS-S-2 and LitS-S-11 enzymes.

Measurement of *L. Italica* Thermostability

Figure 8:
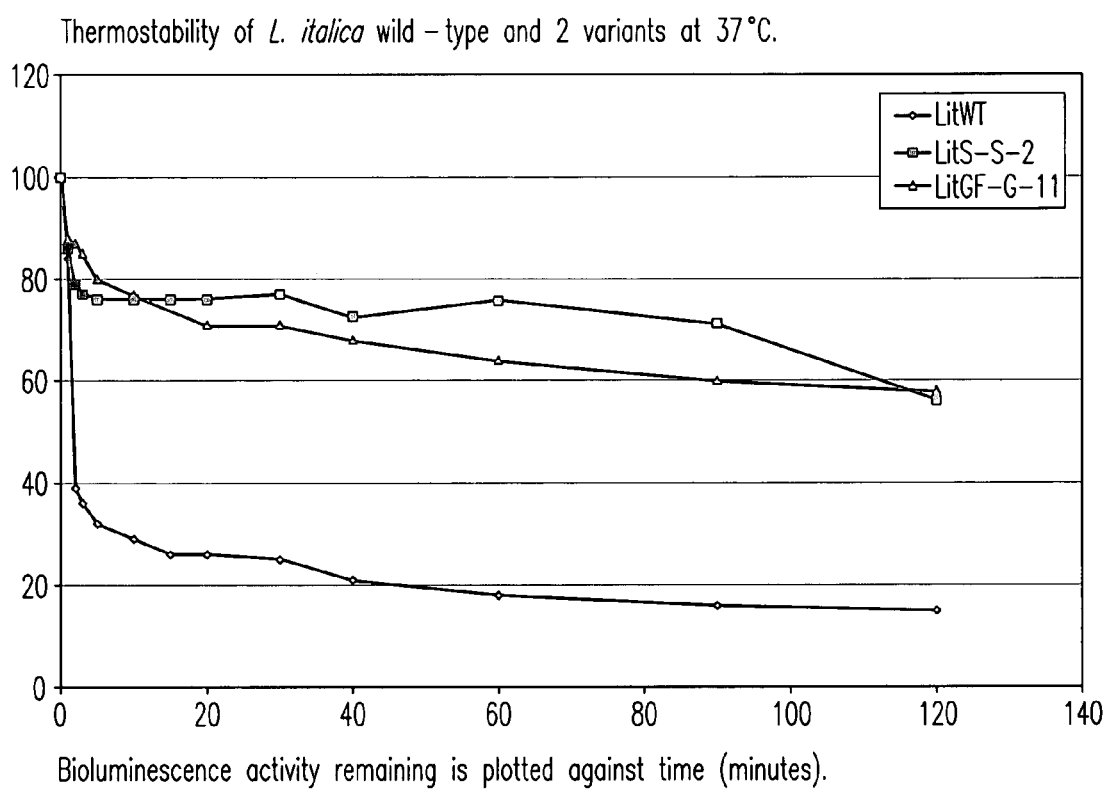
FIG. 8 shows the thermostability of Lit WT and LitS-S-2 and LitGF-G-11.

In a 0.2 mL PCR tube, solutions of 0.1 mg luciferase in 10 µL CBA (50 mM Tris, pH 7.0, 150 mM NaCl, 1 mM EDTA, 1 mM DTT, 0.8M $(NH_4)_2 SO_4$, 2.0% glycerol) and 200 µL 25 mM glycyl-glycine buffer, pH 7.8, were prepared. An aliquot (50 µL) of the solution was reserved on ice. Initial activity values were obtained by flash height activity assays performed on 2-10 µL samples of enzyme. The sample was placed in a thermocycler set at 37° C. Aliquots were withdrawn over an 8 hour period and compared to a controls kept in ice. Thermostability was evaluated by plotting residual flash height activity at 37° C. as a function of time. Half-lives were calculated from the first order rate constant obtained by plotting the ln residual flash height activity versus time. The half-lives of LitWT, LitS-S-2 and LitGF-G-11 were determined as shown in FIGS. 6 and 8.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. An isolated luciferase polypeptide comprising the amino acid sequence of SEQ ID NO:2, except that Gly 216 is changed to Ala, Thr 217 is changed to Leu, Ser 234 is changed to Ala, Ser 286 is changed to Thr, Glu 356 is changed to Lys, Lys 547 is changed to Gly and Met 548 is changed to Gly and wherein said polypeptide produces a bioluminescence emission maximum of approximately 609 nm.

* * * * *